(12) United States Patent
Schwartz

(10) Patent No.: US 8,475,524 B2
(45) Date of Patent: Jul. 2, 2013

(54) MONITORING OF PERCUTANEOUS MITRAL VALVULOPLASTY

(75) Inventor: Yitzhack Schwartz, Haifa (IL)

(73) Assignee: Biosense Webster, Inc., Diamond Bar, CA (US)

( * ) Notice: Subject to any disclaimer, the term of this patent is extended or adjusted under 35 U.S.C. 154(b) by 1582 days.

(21) Appl. No.: 11/194,791

(22) Filed: Aug. 1, 2005

(65) Prior Publication Data

US 2007/0027392 A1 Feb. 1, 2007

(51) Int. Cl.
*A61F 2/24* (2006.01)

(52) U.S. Cl.
USPC .................................. 623/2.36; 623/2.37

(58) Field of Classification Search
CPC ............................................... A61F 2/24
USPC ......................................................... 623/2.36
See application file for complete search history.

(56) References Cited

U.S. PATENT DOCUMENTS

| | | | |
|---|---|---|---|
| 4,821,731 A * | 4/1989 | Martinelli et al. | 600/463 |
| 4,951,677 A * | 8/1990 | Crowley et al. | 600/463 |
| 5,453,575 A * | 9/1995 | O'Donnell et al. | 600/463 |
| 5,524,630 A * | 6/1996 | Crowley | 600/466 |
| 6,029,671 A * | 2/2000 | Stevens et al. | 128/898 |
| 6,083,170 A | 7/2000 | Ben-Haim | |
| 6,332,089 B1 | 12/2001 | Acker et al. | |
| 6,618,612 B1 | 9/2003 | Acker et al. | |
| 6,650,927 B1 | 11/2003 | Keidar | |
| 6,658,279 B2 * | 12/2003 | Swanson et al. | 600/407 |
| 6,676,702 B2 | 1/2004 | Mathis | |
| 6,690,963 B2 | 2/2004 | Ben-Haim et al. | |
| 6,702,777 B2 * | 3/2004 | Haim et al. | 604/66 |
| 6,716,166 B2 | 4/2004 | Govari | |
| 6,773,402 B2 | 8/2004 | Govari et al. | |
| 2002/0065455 A1 | 5/2002 | Ben-Haim et al. | |
| 2002/0095167 A1 | 7/2002 | Liddicoat et al. | |
| 2002/0165448 A1 | 11/2002 | Ben-Haim et al. | |
| 2003/0065271 A1 * | 4/2003 | Khoury | 600/509 |
| 2003/0083538 A1 | 5/2003 | Adams et al. | |
| 2003/0144658 A1 | 7/2003 | Schwartz et al. | |
| 2004/0068178 A1 | 4/2004 | Govari | |

(Continued)

FOREIGN PATENT DOCUMENTS

| | | |
|---|---|---|
| JP | 2004/530484 | 12/2002 |
| JP | 2002/113004 | 4/2004 |
| WO | 2004/012583 A2 | 2/2004 |
| WO | 2004/014282 A2 | 2/2004 |

OTHER PUBLICATIONS

European Search Report (EP 06 25 4007) Dated Sep. 12, 2007.

(Continued)

*Primary Examiner* — Jason-Dennis Stewart
(74) *Attorney, Agent, or Firm* — Louis J. Capezzuto

(57) ABSTRACT

During a minimally invasive deployment of a mitral valvuloplasty device into the coronary sinus near realtime tracking of the device is monitored to determine whether the device is compressing the left circumflex coronary artery or is likely to do so. In one embodiment of the invention, one or more position sensors are included in the catheter that is used to deploy the constricting implant and or in the implant itself. The position of the device is determined during deployment, and compared to the location of the left circumflex coronary artery, which may be determined by mapping relative to a pre-acquired image or by simultaneous intracardiac ultrasound imaging.

6 Claims, 5 Drawing Sheets

U.S. PATENT DOCUMENTS

| | | | |
|---|---|---|---|
| 2004/0097805 A1* | 5/2004 | Verard et al. | 600/428 |
| 2004/0102769 A1 | 5/2004 | Schwartz et al. | |
| 2004/0102840 A1 | 5/2004 | Solem et al. | |
| 2004/0147920 A1 | 7/2004 | Keidar | |
| 2005/0113685 A1 | 5/2005 | Maschke et al. | |
| 2005/0203410 A1* | 9/2005 | Jenkins | 600/459 |
| 2005/0222554 A1* | 10/2005 | Wallace et al. | 606/1 |
| 2006/0241445 A1* | 10/2006 | Altmann et al. | 600/443 |
| 2006/0241465 A1* | 10/2006 | Huennekens et al. | 600/458 |
| 2006/0253032 A1* | 11/2006 | Altmann et al. | 600/466 |
| 2006/0293643 A1* | 12/2006 | Wallace et al. | 606/1 |
| 2007/0043338 A1* | 2/2007 | Moll et al. | 606/1 |

OTHER PUBLICATIONS

MacNab, A., et al., "A Method for the Morphological Analysis of the Regurgitant Mitral Valve Using Three Dimensional Echocardiography", Heart 90:771-776, 2004.

Votta, Emiliano et al.,"3-D Computational Models for the Simulation of Mitral Valve Annuloplasty", Proc. 2003 Summer Bioengineering Conference, Jun. 25-29, Sonesta Beach Resort in Key Biscayne, Florida.

Biosense Webster, Inc., U.S. Appl. No. 11/030,944—pending.

Biosense Webster, Inc., U.S. Appl. No. 11/115,002—pending.

* cited by examiner

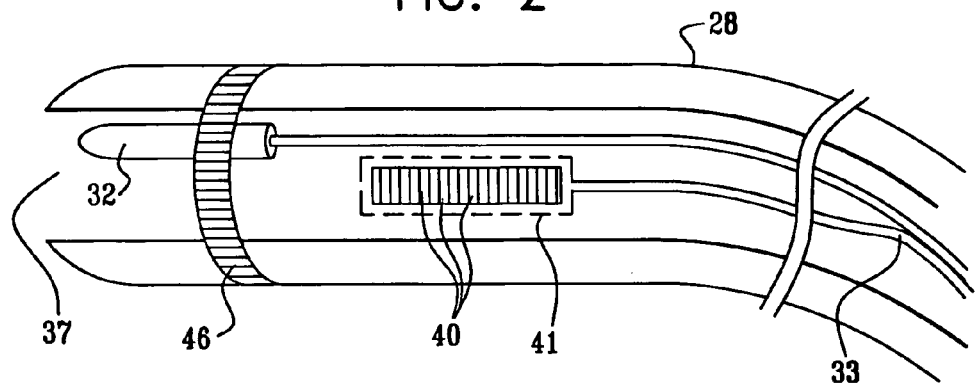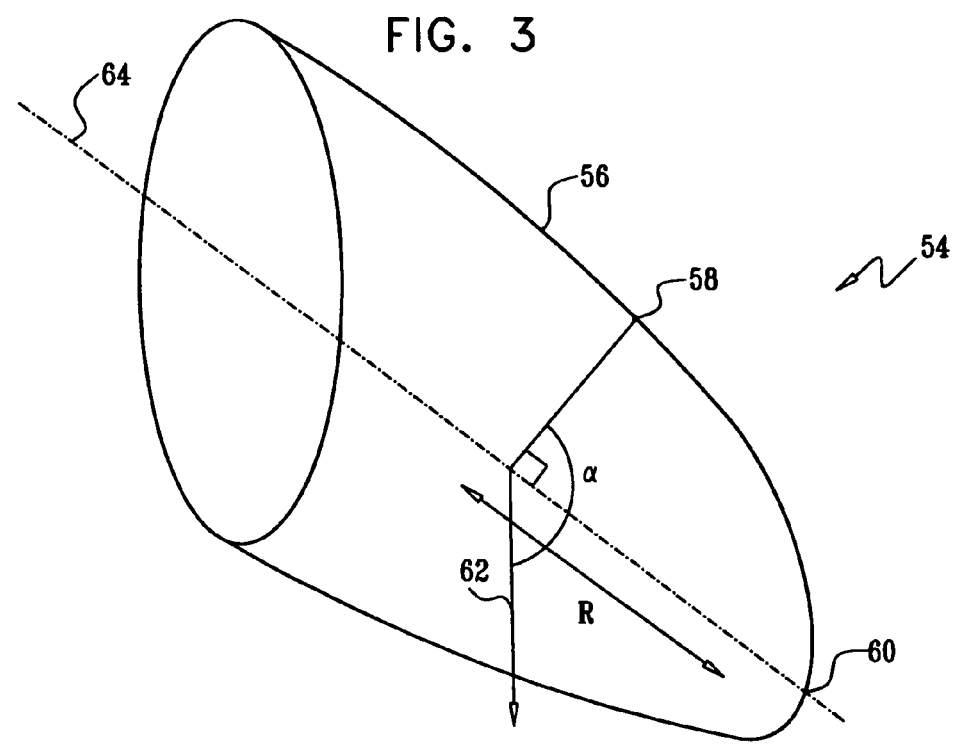

MONITORING OF PERCUTANEOUS MITRAL VALVULOPLASTY

BACKGROUND OF THE INVENTION

1. Field of the Invention

This invention relates to methods and systems for the treatment of valvular disease of the heart. More particularly, this invention relates to monitoring of percutaneous mitral valvuloplasty procedures.

2. Description of the Related Art

A number of different treatments are known or in development to effect minimally invasive mitral valvuloplasty, in order to treat conditions such as mitral regurgitation. One family of solutions takes advantage of the fact that the coronary sinus partially encircles the mitral valve along the atrioventricular groove, generally in the same plane as the mitral valve annulus. A number of companies have developed implants that may be inserted into the coronary sinus and then actuated, typically by mechanical or thermal means to cinch or otherwise constrict the mitral valve annulus. This tends to reduce the radius of curvature of the annulus, which results in improved coaptation of the valve leaflets.

Representative disclosures that exemplify this approach are U.S. Patent Application Publication No. 2003/0083538 and U.S. Pat. No. 6,676,702. Both describe a resilient annuloplasty device, which is percutaneously introduced into the coronary sinus so as to partially encompass the mitral valve annulus. When actuated, the shape of the member is fixed, and it transmits a generally radially directed deforming force on the mitral valve annulus, urging at least a portion of the annulus inwardly.

The left circumflex coronary artery (LCx) runs along the coronary sinus, and at a crossover point it passes under the coronary sinus. The procedures and devices that are currently being employed in the coronary sinus risk compression of the left circumflex coronary artery, and compromise of its blood flow. For example, the above-noted U.S. Pat. No. 6,676,702 cautions that a device placed in the coronary sinus must not be permitted to extend within the coronary sinus beyond the crossover point of the circumflex artery and the coronary sinus to avoid constriction of the left circumflex coronary artery. Even when this precaution is observed, the possibility of aberrant coronary vascular anatomy still creates a risk for the patient.

SUMMARY OF THE INVENTION

According to disclosed embodiments of the invention a mitral valvuloplasty procedure is monitored in near realtime, so that complications can be anticipated and avoided. Using the methods and systems of the invention, the danger of compromising the left circumflex coronary artery by an annuloplasty device implanted in the coronary sinus is averted.

During the implantation procedure, it is determined whether the implant is compressing the left circumflex coronary artery, or is likely to do so. In some embodiments, one or more position sensors are included in a catheter that is used to deploy the annuloplasty device. Additionally or alternatively, sensors can be incorporated in the annuloplasty device itself. The position of the annuloplasty device is determined during implantation and compared to the known location of the left circumflex coronary artery generally, and the crossover with the coronary sinus in particular. The location of the left circumflex coronary artery may be determined by mapping relative to a pre-acquired image or alternatively by near realtime intracardiac ultrasound imaging. If the annuloplasty device is found to be too close to the left circumflex coronary artery, it is repositioned or removed.

In another embodiment, an ultrasound catheter is used to image the left circumflex coronary artery and/or to visualize blood flow therein using Doppler imaging.

The invention provides a method of deforming a mitral valve annulus in a heart of a living subject, which is carried out by constructing an anatomic image of at least a portion of the heart, and inserting a deployment catheter into the coronary sinus. Using the deployment catheter, the method is further carried out by positioning an annuloplasty device into an operative location in the coronary sinus, and registering the operative location of the annuloplasty device with the anatomic image. The method is further carried out by determining that actuation of the annuloplasty device in the operative location is unlikely to compromise blood flow in the left circumflex coronary artery of the heart, and thereafter actuating the annuloplasty device to deform the annulus.

In one aspect of the method, constructing an anatomic image comprises inserting an ultrasound catheter having ultrasound transducers into the heart, using the ultrasound catheter to obtain a plurality of 2-dimensional ultrasound images of the heart, and combining the 2-dimensional ultrasound images into a 3-dimensional ultrasound image.

Another aspect of the method comprises ascertaining that the annuloplasty device avoids a crossover of the coronary sinus with the left circumflex coronary artery.

In a further aspect of the method, the anatomic image is constructed prior to inserting the deployment catheter.

In yet another aspect of the method, the anatomic image is constructed concurrently with insertion of the deployment catheter.

In still another aspect of the method, subsequent to actuating the annuloplasty device, and while the deployment catheter remains in the heart, blood flow in the left circumflex coronary artery is measured.

In an additional aspect of the method, blood flow in the left circumflex coronary artery is measured by Doppler imaging of the left circumflex coronary artery.

In one aspect of the method, mitral valve blood flow is measured subsequent to actuating the annuloplasty device, and while the deployment catheter remains in the heart.

In another aspect of the method, constructing an anatomic image comprises acquiring the anatomic image using the deployment catheter.

One aspect of the method includes the further step of directing ablative energy onto a portion of the heart to disrupt electrical conduction therein.

The invention provides an apparatus for performing percutaneous mitral valvuloplasty, including a deployment catheter adapted to insert an annuloplasty device into a coronary sinus of a heart in a living subject. The deployment catheter is operative for actuating the annuloplasty device in an operative location in the coronary sinus. The apparatus includes a location positioning system having an image processor and a mapping catheter for acquiring an anatomic image of a portion of the heart. The location positioning system is operative for registering the operative location of the annuloplasty device with the anatomic image while the annuloplasty device is inserted by the deployment catheter. The location positioning system is operative for locating points of interest on the left circumflex coronary artery of the heart, whereby an operator can determine whether actuation of the annuloplasty device in the operative location may comprise blood flow through the left circumflex coronary artery.

An aspect of the apparatus includes an ultrasound driver in the location positioning system, wherein the mapping catheter is an ultrasound catheter having ultrasound transducers. Acoustic signals received by the ultrasound transducers are transmitted to the image processor, which is operative for constructing a plurality of 2-dimensional ultrasound images of the heart, and combining the 2-dimensional ultrasound images into a 3-dimensional ultrasound image.

The invention provides an apparatus for performing percutaneous mitral valvuloplasty, including a catheter adapted for insertion of an annuloplasty device into the coronary sinus of a heart in a living subject. The catheter is operative for actuating the annuloplasty device in an operative location in the coronary sinus. The catheter has ultrasound transducers adapted for transmitting first acoustic signals toward the heart and receiving second acoustic signals that are echoes of the first acoustic signals. The apparatus includes a location positioning system having an ultrasound driver for driving the transducers, and an image processor for receiving electrical signals from the ultrasound transducers of the catheter and processing the signals to construct an anatomic image of a portion of the heart. The location positioning system is operative for registering the location of the annuloplasty device with the anatomic image while the annuloplasty device is being inserted by the catheter. The location positioning system is operative for locating points of interest on the left circumflex coronary artery of the heart, whereby an operator can determine whether actuation of the annuloplasty device may comprise blood flow through the left circumflex coronary artery.

BRIEF DESCRIPTION OF THE DRAWINGS

For a better understanding of the present invention, reference is made to the detailed description of the invention, by way of example, which is to be read in conjunction with the following drawings, wherein like elements are given like reference numerals, and wherein:

FIG. 2 schematically illustrates an embodiment of the distal end of a catheter used in the system shown in FIG. 1, in accordance with a disclosed embodiment of the invention;

FIG. 3 is a simplified geometric representation of an image of a heart, which has been prepared for registration with another diagnostic image or with a catheter being positioned in accordance with a disclosed embodiment of the invention;

DETAILED DESCRIPTION OF THE INVENTION

In the following description, numerous specific details are set forth in order to provide a thorough understanding of the present invention. It will be apparent to one skilled in the art, however, that the present invention may be practiced without these specific details. In other instances, well-known circuits, control logic, and the details of computer program instructions for conventional algorithms and processes have not been shown in detail in order not to obscure the present invention unnecessarily.

Software programming code, which embodies aspects of the present invention, is typically maintained in permanent storage, such as a computer readable medium. In a client-server environment, such software programming code may be stored on a client or a server. The software programming code may be embodied on any of a variety of known media for use with a data processing system. This includes, but is not limited to, magnetic and optical storage devices such as disk drives, magnetic tape, compact discs (CD's), digital video discs (DVD's), and computer instruction signals embodied in a transmission medium with or without a carrier wave upon which the signals are modulated. For example, the transmission medium may include a communications network, such as the Internet. In addition, while the invention may be embodied in computer software, the functions necessary to implement the invention may alternatively be embodied in part or in whole using hardware components such as application-specific integrated circuits or other hardware, or some combination of hardware components and software.

System Overview

Figure 1:
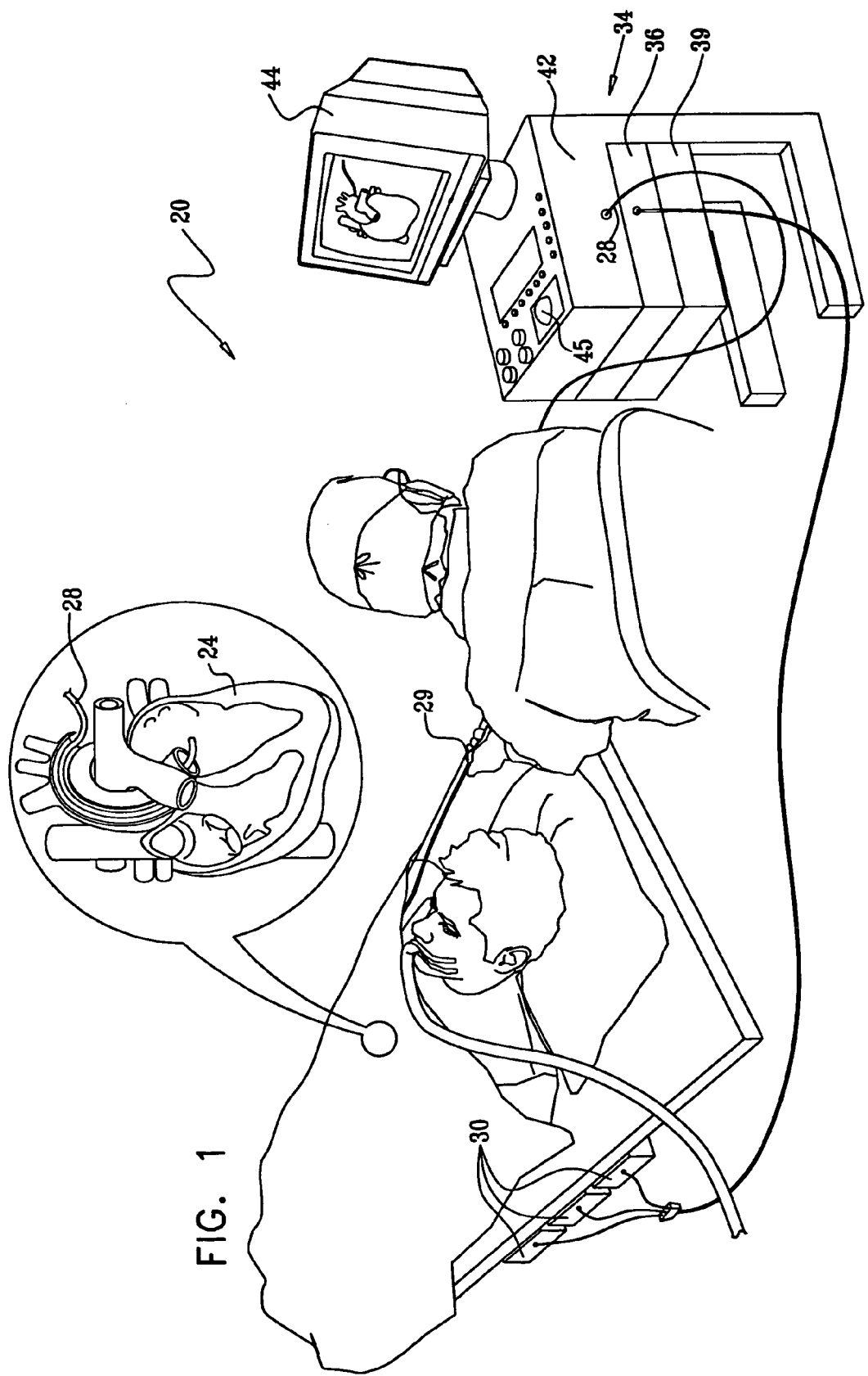
FIG. 1 is a schematic of a system for imaging and mapping a heart of a patient during therapeutic procedures, in accordance with a disclosed embodiment of the invention.

Turning now to the drawings, reference is initially made to FIG. 1, which is an illustration of a system 20 for imaging and mapping a heart 24 of a patient, and which is suitable for performing therapeutic procedures involving the deployment of annuloplasty devices in the heart 24 or its vasculature, in accordance with a disclosed embodiment of the invention. The system comprises a catheter 28, which is percutaneously inserted by a physician into a chamber or vascular structure of the heart, e.g., the coronary sinus. The catheter 28 typically comprises a handle 29 for operation of the catheter by the physician. Suitable controls on the handle enable the physician to steer, position and orient the distal end of the catheter as desired.

The system 20 comprises a positioning subsystem that measures location and orientation coordinates of the catheter 28. Throughout this patent application, the term "location" refers to the spatial coordinates of the catheter, and the term "orientation" refers to its angular coordinates. The term "position" refers to the full positional information of the catheter, comprising both location and orientation coordinates.

In one embodiment, the positioning subsystem comprises a magnetic position tracking system that determines the position and orientation of the catheter 28. The positioning subsystem generates magnetic fields in a predefined working volume its vicinity and senses these fields at the catheter. The positioning subsystem typically comprises a set of external radiators, such as field generating coils 30, which are located in fixed, known positions external to the patient. The coils 30 generate fields, typically electromagnetic fields, in the vicinity of the heart 24. The generated fields are sensed by a position sensor 32 inside the catheter 28.

In an alternative embodiment, a radiator in the catheter, such as a coil, generates electromagnetic fields, which are received by sensors outside the patient's body.

The position sensor transmits, in response to the sensed fields, position-related electrical signals over cables 33 running through the catheter to a console 34. Alternatively, the position sensor may transmit signals to the console over a wireless link. The console comprises a positioning processor 36 that calculates the location and orientation of the catheter 28 based on the signals sent by position sensor 32. The positioning processor 36 typically receives, amplifies, filters, digitizes, and otherwise processes signals from the catheter 28.

Some position tracking systems that may be used for this purpose are described, for example, in U.S. Pat. Nos. 6,690, 963, 6,618,612 and 6,332,089, and U.S. Patent Application Publications 2002/0065455 A1, 2004/0147920 A1 and 2004/0068178 A1, whose disclosures are all incorporated herein by reference. Although the positioning subsystem shown in FIG. 1 uses magnetic fields, the methods described below may be implemented using any other suitable positioning subsystem, such as systems based on electromagnetic fields, acoustic or ultrasonic measurements.

Alternatively, the system 20 can be realized as the Carto-Biosense® Navigation System, available from Biosense Webster, Inc., 3333 Diamond Canyon Road, Diamond Bar, Calif. 91765, suitably modified to execute the procedures described hereinbelow. For example, the system 20 may be adapted, mutatis mutandis, to employ the catheters disclosed in the above-noted U.S. Pat. Nos. 6,716,166 and 6,773,402 in order to acquire ultrasound images for display in near real-time ultrasound images concurrently with an image or representation of the position of a deployment catheter in the same or different sessions, and in many different combinations.

When used for inserting therapy devices and implants, the catheter 28 is provided with a flexible guide wire, which is fed into a desired site in the coronary sinus of the heart. Additionally or alternatively, in different embodiments of the catheter 28, a flexible guide (not shown) is provided, and is adapted for feeding into the coronary sinus of the heart over the guide wire. Accessory ports, such as a side port (not shown) may optionally be provided to accommodate the requirements for deploying particular implants and therapy devices.

Reference is now made to FIG. 2, which schematically illustrates an embodiment of the distal end of the catheter 28 (FIG. 1), in accordance with an embodiment of the present invention. The catheter 28 comprises an ultrasonic imaging sensor. The ultrasonic sensor typically comprises an array of ultrasonic transducers 40. In one embodiment, the transducers are piezo-electric transducers. The ultrasonic transducers are positioned in or adjacent to a window 41, which defines an opening within the body or wall of the catheter. The catheter 28 typically has at least one lumen 37, which can admit a guide wire and guide tube to aid in deployment of a therapeutic valvuloplasty device.

The transducers 40 operate as a phased array, jointly transmitting an ultrasound beam from the array aperture through the window 23. Although the transducers are shown arranged in a linear array configuration, other array configurations can be used, such as circular or convex configurations. In one embodiment, the array transmits a short burst of ultrasound energy and then switches to a receiving mode for receiving the ultrasound signals reflected from the surrounding tissue. Typically, the transducers 40 are driven individually in a controlled manner in order to steer the ultrasound beam in a desired direction. By appropriate timing of the transducers, the produced ultrasound beam can be given a concentrically curved wave front, so as to focus the beam at a given distance from the transducer array. Thus, the system 20 (FIG. 1) uses the transducer array as a phased array and implements a transmit/receive scanning mechanism that enables the steering and focusing of the ultrasound beam, so as to produce two-dimensional ultrasound images.

In one embodiment, the ultrasonic sensor comprises between sixteen and sixty-four transducers 40, preferably between forty-eight and sixty-four transducers. Typically, the transducers generate the ultrasound energy at a center frequency in the range of 5-10 MHz, with a typical penetration depth of 14 cm. The penetration depth typically ranges from several millimeters to around 16 centimeters, and depends upon the ultrasonic sensor characteristics, the characteristics of the surrounding tissue and the operating frequency. In alternative embodiments, other suitable frequency ranges and penetration depths can be used.

After receiving the reflected ultrasound echoes, electric signals based on the reflected acoustic signals or echoes are sent by transducers 40 over cables 33 through the catheter 28 to an image processor 42 (FIG. 1) in the console 34, which transforms them into two-dimensional, typically sector-shaped ultrasound images. The image processor 42 typically computes or determines position and orientation information, displays real-time ultrasound images, performs three-dimensional image or volume reconstructions and other functions, which will all be described in greater detail below.

In some embodiments, the image processor uses the ultrasound images and the positional information to produce a three-dimensional model of a target structure of the patient's heart. The three-dimensional model is presented to the physician as a two-dimensional projection on a display 44.

In some embodiments, the distal end of the catheter also comprises at least one electrode 46 for performing diagnostic functions, therapeutic functions or both, such as electrophysiological mapping and radio frequency (RF) ablation. In one embodiment, the electrode 46 is used for sensing local electrical potentials. The electrical potentials measured by the electrode 46 may be used in mapping the local electrical activity on the endocardial surface. When the electrode 46 is brought into contact or proximity with a point on the inner surface of the heart 24 (FIG. 1), it measures the local electrical potential at that point. The measured potentials are converted into electrical signals and sent through the catheter to the image processor for display. In other embodiments, the local electrical potentials are obtained from another catheter comprising suitable electrodes and a position sensor, all connected to the console 34. In some applications, the electrode 46 can be used to determine when the catheter is in contact with a valve, since the electrical potentials are weaker there than in the myocardium.

Although the electrode 46 is shown as being a single ring electrode, the catheter may comprise any number of electrodes in any form. For example, the catheter may comprise two or more ring electrodes, a plurality or array of point electrodes, a tip electrode, or any combination of these types of electrodes for performing the diagnostic and therapeutic functions outlined above.

The position sensor 32 is typically located within the distal end of the catheter 28, adjacent to the electrode 46 and the transducers 40. Typically, the mutual positional and orientational offsets between the position sensor 32, electrode 46 and transducers 40 of the ultrasonic sensor are constant. These offsets are typically used by the positioning processor 36 to derive the coordinates of the ultrasonic sensor and of the electrode 46, given the measured position of the position sensor 32. In another embodiment, the catheter 28 comprises two or more position sensors 32, each having constant positional and orientational offsets with respect to the electrode 46 and the transducers 40. In some embodiments, the offsets (or equivalent calibration parameters) are pre-calibrated and stored in the positioning processor 36. Alternatively, the offsets can be stored in a memory device (such as an electrically programmable read-only memory, or EPROM) fitted into the handle 29 of the catheter 28.

The position sensor 32 typically comprises three non-concentric coils (not shown), such as described in U.S. Pat. No. 6,690,963, cited above. Alternatively, any other suitable position sensor arrangement can be used, such as sensors comprising any number of concentric or non-concentric coils, Hall-effect sensors or magneto-resistive sensors.

Typically, both the ultrasound images and the position measurements are synchronized with the heart cycle, by gating signal and image capture relative to a body-surface electrocardiogram (ECG) signal or intra-cardiac electrocardiogram. (In one embodiment, the ECG signal can be produced by the electrode 46.) Since features of the heart change their shape and position during the heart's periodic contraction and relaxation, the entire imaging process is typically performed at a particular timing with respect to this period. In some embodiments, additional measurements taken by the catheter, such as measurements of various tissue characteristics, temperature and blood flow measurements, are also synchronized to the electrocardiogram (ECG) signal. These measurements are also associated with corresponding position measurements taken by the position sensor 32. The additional measurements are typically overlaid on the reconstructed three-dimensional model, as will be explained below.

In some embodiments, the position measurements and the acquisition of the ultrasound images are synchronized to an internally generated signal produced by the system 20. For example, the synchronization mechanism can be used to avoid interference in the ultrasound images caused by a certain signal. In this example, the timing of image acquisition and position measurement is set to a particular offset with respect to the interfering signal, so that images are acquired without interference. The offset can be adjusted occasionally to maintain interference-free image acquisition. Alternatively, the measurement and acquisition can be synchronized to an externally supplied synchronization signal.

In one embodiment, the system 20 comprises an ultrasound driver 39 that drives the ultrasound transducers 40. One example of a suitable ultrasound driver, which can be used for this purpose is an AN2300™ ultrasound system produced by Analogic Corp. (Peabody, Mass.). In this embodiment, the ultrasound driver performs some of the functions of the image processor 42, driving the ultrasonic sensor and producing the two-dimensional ultrasound images. The ultrasound driver may support different imaging modes such as B-mode, M-mode, CW Doppler and color flow Doppler, as are known in the art.

Typically, the positioning and image processors are implemented using a general-purpose computer, which is programmed in software to carry out the functions described herein. The software may be downloaded to the computer in electronic form, over a network, for example, or it may alternatively be supplied to the computer on tangible media, such as CD-ROM. The positioning processor and image processor may be implemented using separate computers or using a single computer, or may be integrated with other computing functions of the system 20. Additionally or alternatively, at least some of the positioning and image processing functions may be performed using dedicated hardware.

2-Dimensional Anatomic Imaging

Referring again to FIG. 1, gated images of the heart are created, e.g., ultrasound, SPECT, images and correlated with location data of the catheter 28. The gated images can be registered with another image, or with the position of the same or a different catheter used for deployment of a therapeutic device in the coronary sinus. Suitable registration techniques are disclosed in U.S. Pat. No. 6,650,927, of common assignee herewith, and herein incorporated by reference. The technique is briefly described:

Reference is now made to FIG. 3, which is a simplified geometric representation of an image 54 of the heart, which has been prepared for registration with another diagnostic image or a catheter positioned in accordance with a disclosed embodiment of the invention. Details of the preparation of the image 54 are described in further detail hereinbelow. A surface 56 corresponds approximately to the surface of the heart. A coordinate system is defined, in which each point 58 on the surface 56 is represented by a distance R from an apex 60 and an angle a relative to a downward direction 62 (i.e., ventrally and caudad relative to the subject 26 (FIG. 1). In order to register another structure with the image 54, an axis 64 and the apex 60 are identified on the image 54 and aligned with corresponding positions, landmarks or fiducial marks of the structure to be registered, using location information provided by the sensors on the catheter 28 (FIG. 1). This is preferably automatic, but additionally or alternatively can be done or assisted by an operator. The scale of the structure to be registered is adjusted so that its dimensions match that of the image 54 as closely as possible.

Figure 4:
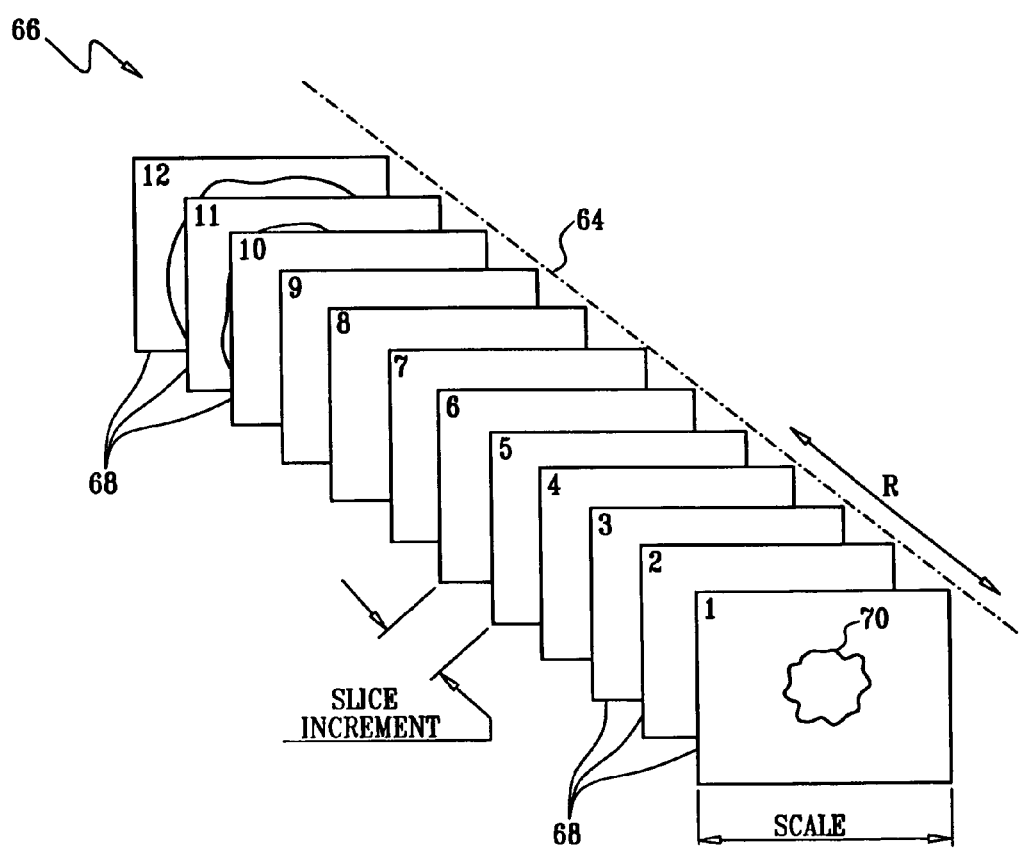
FIG. 4 is a schematic exploded view of a diagnostic image of a heart for use in the system shown in FIG. 1, in accordance with a disclosed embodiment of the invention.

Reference is now made to FIG. 4, which is a schematic exploded view of a diagnostic image 66 of the heart 24 (FIG. 1), in accordance with a disclosed embodiment of the invention. The view is generated using a bullseye rendition technique. The image 66 comprises a stack of parallel slices 68, which are perpendicular to the axis 64. The slices are typically taken at a fixed slice increment along the axis 64. Each slice shows a section 70.

3-Dimensional Anatomic Imaging

Referring again to FIG. 1, three-dimensional imaging is described in commonly assigned application Ser. No. 11/115, 002, filed on Apr. 26, 2005, entitled "Three-Dimensional Cardiac Imaging Using Ultrasound Contour Reconstruction", which is herein incorporated by reference. A brief description of the method will facilitate understanding of the present invention.

Essentially, the disclosed method combines multiple two-dimensional ultrasound images, acquired at different positions of the catheter 28 as described above, into a single three-dimensional model of the target structure. Typically, the physician inserts the catheter 28 through a suitable blood vessel into a chamber of the heart, and then scans the target structure by moving the catheter between different positions inside the chamber. In each catheter position, the image processor 42 acquires and produces a two-dimensional ultrasound image, Referring again to FIG. 1, during deployment of a therapeutic device or implant, the positioning subsystem of the system 20 measures and calculates the current position of the catheter 28. The calculated position is stored together with the corresponding slice or slices 68 (FIG. 3). Typically, each position of the catheter 28 is represented in coordinate form, such as a six-dimensional coordinate (X, Y, Z axis positions, and pitch, yaw and roll angular orientations).

The image processor 42 subsequently assigns three-dimensional coordinates to contours of interest that are identified in the set of images. The location and orientation of the planes of these images in three-dimensional space are known by virtue of the positional information, stored together with the images. Therefore, the image processor is able to determine the three-dimensional coordinates of any pixel in the two-dimensional images. When assigning the coordinates, the image processor typically uses stored calibration data comprising position and orientation offsets between the position sensor and the ultrasonic sensor, as described above.

Alternatively, the system 20 (FIG. 1) can be used for three-dimensional display and projection of two-dimensional ultrasound images, without reconstructing a three-dimensional model. For example, the physician can acquire a single two-dimensional ultrasound image, and tag contours of interest on this image, e.g., the coronary sinus. The system 20 can then orient and project the ultrasound image in three-dimensional space. During a medical procedure the system can continuously track and display the three-dimensional position of the catheter performing the medical procedure, which may be different from the catheter that acquired the image onto which the catheter now performing the medical procedure is being registered.

Alternative Embodiments

In yet another embodiment of the invention, Doppler flow imaging of the left circumflex coronary artery by well known techniques is conducted concurrently with the deployment of a therapeutic device in the coronary sinus. Both the flow images and the catheter position are registered with a previously acquired two-dimensional or three-dimensional image of the heart, as described above.

In still other embodiments of the invention, preacquired anatomic images, and the determination of cardiac locations of interest, e.g., the coronary sinus, are obtained using non-invasive imaging methods, i.e., cardiac CT or MR imaging, cardiac neurotransmission imaging using SPECT and PET, or can be found using epicardial electrical maps. These locations are then displayed on maps or images of the heart, and thus targeted for minimally invasive or noninvasive therapy.

A large proportion of patients requiring mitral valvuloplasty also suffer from atria arrhythmias, particularly atrial fibrillation. Ablative therapy can be conveniently performed during the same session as valvuloplasty, for example using the ultrasound and radiofrequency ablative techniques described in commonly assigned U.S. Patent Application Publication Nos. 2003/0144658 and 2004/0102769, which are herein incorporated by reference. Other known ablative techniques may also be used. Briefly, these techniques involve the creation of lesions by directing ablative energy into the wall of the cardiac atria or pulmonary vein ostia, resulting in disruption of undesirable electrical conductive pathways.

Operation

Figure 5:
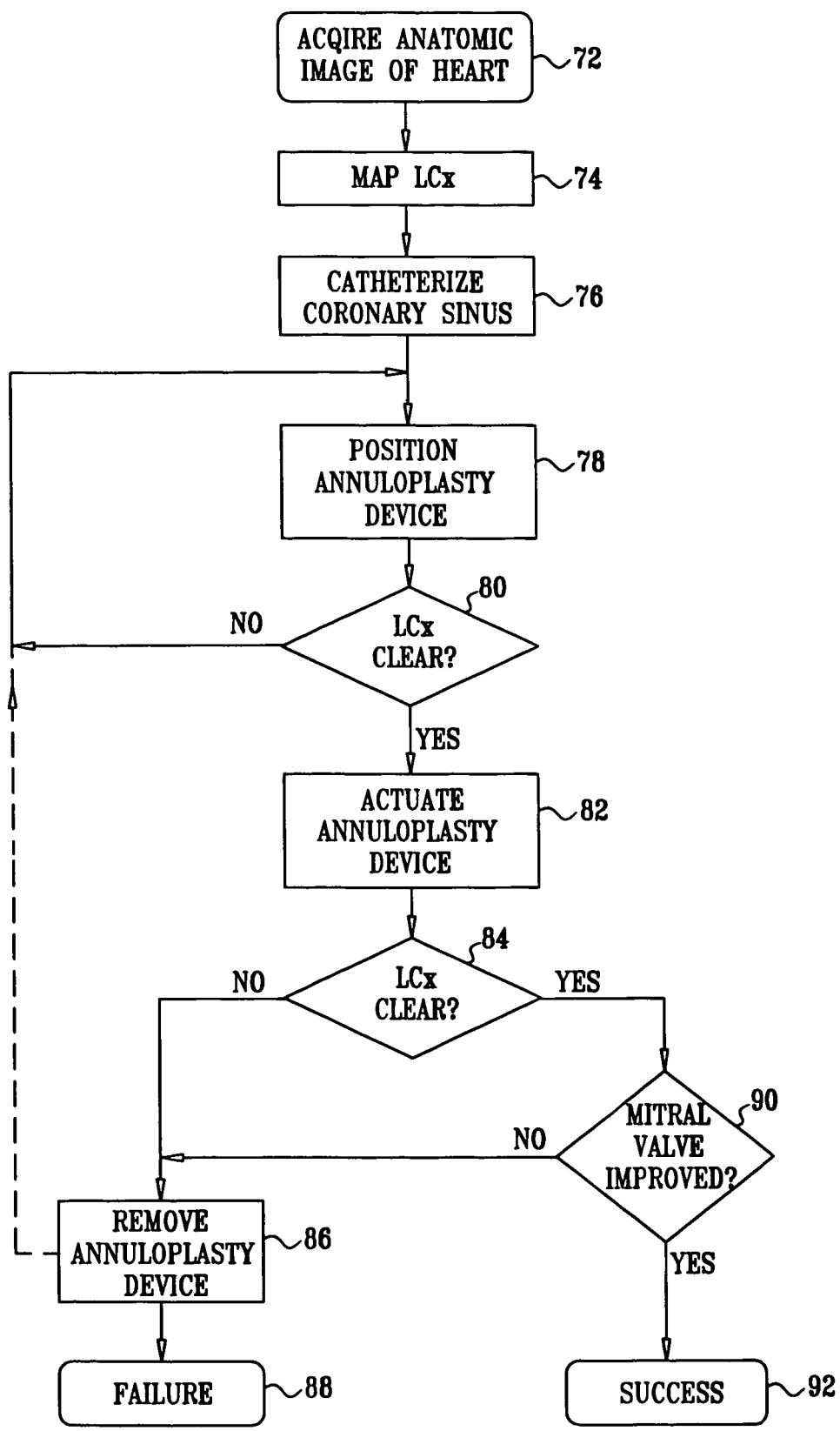
FIG. 5 is a flow chart illustrating a method of monitoring a percutaneous mitral valvuloplasty procedure in accordance with a disclosed embodiment of the invention.

Reference is now made to FIG. 5, which is a flow chart illustrating a method of monitoring a percutaneous mitral valvuloplasty procedure in accordance with a disclosed embodiment of the invention. At initial step 72, an anatomic image of the heart is acquired. In one embodiment this is a three-dimensional ultrasound image acquired using percutaneous cardiac catheterization, as described above. Location coordinates of the coronary sinus and the left circumflex coronary artery are noted, including the coordinates of the crossover of the coronary sinus and the left circumflex coronary artery. Alternatively, the anatomic image can be acquired using any of the other techniques described above. In any case, the images are intended to be registered with new data obtained while deploying a valvuloplasty device. At this point, it is often convenient to study the anatomic image in order to select a therapeutic annuloplasty device. Selection is typically based on a measurement of the diameter of the mitral valve annulus, and an evaluation of the anatomy of the coronary sinus. Additionally, the anatomy of the left circumflex coronary artery and its relationship with the coronary sinus can be evaluated on the image in order to plan an optimal placement of the annuloplasty device in the coronary sinus.

Optionally, prior to its insertion, a model and simulation of the selected annuloplasty device may be conducted, and its effects when deployed can be predicted. Information provided by the simulation improves the procedure, as well as the post-implantation evaluation of the procedure. Applicable techniques for modeling and simulation are disclosed in the documents 3-*D Computational Models for the Simulation of Mitral Valve Annuloplasty*, Votta, Emiliano et al., in Proc. 2003 Summer Bioengineering Conference, Sonesta Beach Resort in Key Biscayne, Fla., Jun. 25-29, 2003; and *A Method for the Morphological Analysis of the Regurgitant Mitral Valve Using Three Dimensional Echocardiography* Macnab, A., et al., Heart 90:771-776, 2004.

Next, at optional step 74, if not already adequately known from initial step 72 or from prior studies of the subject's anatomy, a guidewire is be inserted into the left circumflex coronary artery, and its course can be precisely mapped. An impedance detection system, which is described in U.S. patent application Ser. No. 11/030,944, filed Jan. 7, 2005, which is assigned to the assignee of the present patent application and whose disclosure is incorporated herein by reference, is suitable for mapping the left circumflex coronary artery in this step. Alternatively, angiographic images can be imported and registered as described above.

Next, at step 76, the coronary sinus is accessed, using the same or a different catheter or probe than was used in initial step 72. Typically this step is performed by first advancing a catheter having position sensors into the coronary sinus. During the introduction of the catheter, its current position is tracked in near realtime, using a position tracking system as described above. The location of the catheter is displayed in registration with the anatomic image that was acquired in initial step 72. The display is adjusted by the physician during the procedure as necessary to change the angle of observation, to zoom in and out, and otherwise manipulate the displayed images to show the catheter advantageously in relation to cardiac structures.

During the performance of step 76 and in subsequent stages of the procedure, the course of the left circumflex coronary artery and its absolute distance from the coronary sinus can be depicted by an ultrasound catheter or guidewire that is alternately inserted and retracted within the coronary sinus. In some embodiments imaging sensors are incorporated into the delivery mechanism of the annuloplasty device, and used for continuously gauging changes in the distance between the left circumflex coronary artery and the coronary sinus using the location positioning techniques described above, and for dynamically evaluating changes in blood flow within the coronary artery, by echo-Doppler imaging. The images are also used to verify the optimal location of the annuloplasty device and the end result, after which the imaging wire or catheter is withdrawn. Further details of this process are presented hereinbelow.

Next, at step 78 a generic annuloplasty device is introduced into the coronary sinus. The details of step 78 vary according to the particular annuloplasty device being employed. In some cases, the annuloplasty device is deployed directly through the catheter. In other cases, a guide wire is advanced through the catheter to the coronary sinus. Then a guide tube is advanced through the lumen of the catheter over the guide wire. Often an introducer, to which the annuloplasty device is attached, is inserted along the guidewire within the guide tube into the mitral valve. In some embodiments, the annuloplasty device also is provided with position sensors, and its position can be directly tracked. In other embodiments, the current location of the annuloplasty device is calculated from its current offset with the distal end of the catheter. Baseline flow measurements of the left circumflex coronary artery may be taken at this point.

Next, at decision step 80, reference is made to the current location of the annuloplasty device relative to the left circumflex coronary artery and it is determined whether actuation of the annuloplasty device would be unlikely to compromise the artery. In particular, as noted above, the annuloplasty device should be positioned such that when it is actuated, it does not exert pressure against the point of crossover with the left circumflex coronary artery.

If the determination at decision step 80 is negative, then control returns to step 78 for adjustment of the position of the annuloplasty device.

If the determination at decision step 80 is affirmative, then control proceeds to step 82. The annuloplasty device is actuated to assume a deployed state. Actuation may occur in different ways. For example, for some stent devices, traction may be exerted on a portion of the stent in a manner described in U.S. Patent Application Publication No. 2004/0102840, which is herein incorporated by reference. Alternatively, the annuloplasty device could be formed of nitinol or another shape memory material, expanded into a deployed condition using a balloon, as is known in the art, and then heat-treated. This type of actuation is described in U.S. Patent Application Publication No. 2003/0083538, which is herein incorporated by reference.

Control now proceeds to decision step 84, where it is determined if blood flow in the left circumflex coronary artery is satisfactory following actuation of the annuloplasty device in step 82. This determination can be made with using conventional methods of evaluating coronary blood flow. Preferably, concurrent echo Doppler flow imaging of the left circumflex coronary artery is performed and may be compared to the baseline flow measurements taken prior to actuation of the annuloplasty device.

If the determination at decision step 84 is negative, control proceeds to step 86, where it may be necessary to remove the annuloplasty device. The procedure ends in failure at final step 88, at which the catheter is withdrawn. Alternatively, as indicated by a broken line in FIG. 5, control may return to step 78 for another attempt to position the same or a different annuloplasty device.

If the determination at decision step 84 is affirmative, then optionally it may be determined at decision step 90 whether the annuloplasty device has successfully ameliorated mitral valvular insufficiency. Preferably, this determination is made intraoperatively by measuring blood flow through the mitral valve using a Doppler ultrasound catheter as is known in the art.

If the determination at decision step 84 is negative, then control proceeds to step 86 or optionally control may return to step 78 for another valvuloplasty attempt.

If the determination at decision step 84 is affirmative, and in embodiments in which decision step 84 is not performed, control proceeds to final step 92. The catheter is withdrawn and the procedure terminates successfully.

EXAMPLE

Figure 6:
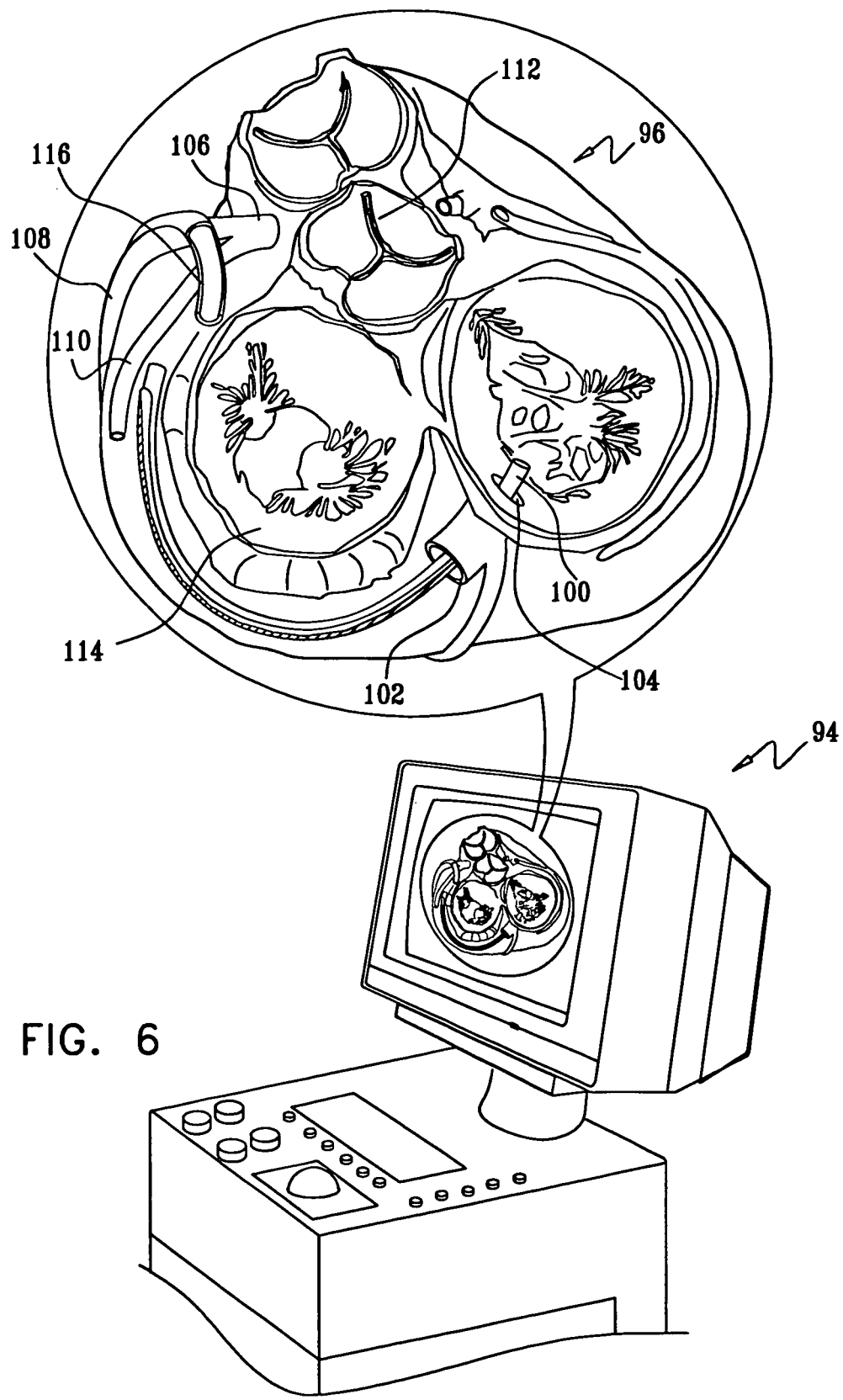
FIG. 6 is a screen display of a cut-away processed image of the superior aspect of a heart in registration with an image of an annuloplasty device during deployment thereof, in accordance with a disclosed embodiment of the invention.

Reference is now made to FIG. 6, which is a screen display 94 illustrating a cut-away processed view of the superior aspect of a heart 96 in registration with an image of an annuloplasty device 98 that would be deployed using a catheter 100 in accordance with a disclosed embodiment of the invention. The great vessels and upper portions of the atria are removed. The image of the heart may be pre-acquired using one of the anatomic imaging techniques and the location positioning system described above, then processed and enhanced by an image processor. Alternatively, the image of the heart may be acquired during deployment of the catheter 100 using the catheter 28 as shown in FIG. 1. The images of the annuloplasty device 98 and catheter 100 are constructed intraoperatively, for example using the system 20 (FIG. 1). Features of the heart 96 that are visible on FIG. 6 include its coronary sinus 102 and ostium 104, left main coronary artery 106, anterior descending branch 108, left circumflex coronary artery 110, aortic valve 112, mitral valve 114, and a crossover 116 of the coronary sinus 102 and left circumflex coronary artery 110. The catheter 100 is shown inserted through the ostium 104, carrying the annuloplasty device 98 thereon. It will be noted that the annuloplasty device 98 lies within the coronary sinus 102, but does not extend to the crossover 116.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. An apparatus for performing percutaneous mitral valvuloplasty, comprising:

a deployment catheter adapted to insert an annuloplasty device into a coronary sinus of a heart in a living subject, said deployment catheter being operative for actuating said annuloplasty device in an operative location in said coronary sinus; and a location positioning system comprising an image processor and a mapping catheter for acquiring an anatomic image of a portion of said heart and a positioning subsystem, said positioning subsystem generating magnetic fields in a predefined working volume, said mapping catheter comprising a position sensor for sensing the magnetic fields at the mapping catheter within the predefined working volume and for transmitting signals indicative of location and orientation coordinates of said mapping catheter and an array of ultrasonic transducers driven in a controlled manner in order to steer an ultrasonic beam in a desired direction for obtaining the anatomic image of the portion of said heart, said location positioning system being operative for registering said operative location of said annuloplasty device with said anatomic image while said annuloplasty device is being inserted by said deployment catheter using location and orientation coordinates, said location positioning system being operative for locating points of interest on a left circumflex coronary artery of said heart whereby an operator can determine whether actuation of said annuloplasty device in said operative location may compromise blood flow through said left circumflex coronary artery.

2. The apparatus according to claim 1, further comprising an ultrasound driver in said location positioning system, wherein said mapping catheter is an ultrasound catheter and the array of ultrasound transducers, uses acoustic signals received by said ultrasound transducers being transmitted to said image processor, said image processor being operative for constructing a plurality of 2-dimensional ultrasound images of said heart, and combining said 2-dimensional ultrasound images into a 3-dimensional ultrasound image.

3. The apparatus according to claim 1, wherein said location positioning system is operative for constructing said anatomic image while said deployment catheter is being inserted.

4. An apparatus for performing percutaneous mitral valvuloplasty, comprising:
 a catheter adapted to insert an annuloplasty device into a coronary sinus of a heart in a living subject, said catheter being operative for actuating said annuloplasty device in an operative location in said coronary sinus, wherein said catheter has ultrasound transducers adapted for transmitting first acoustic signals toward said heart and receiving second acoustic signals that are echoes of said first acoustic signals, and wherein said catheter has a position sensor for sensing magnetic fields at the catheter within a predefined working volume and for transmitting signals indicative of location and orientation coordinates of said catheter,
 a location positioning system comprising a positioning subsystem for generating the magnetic fields in the predefined working volume, an ultrasound driver for driving said transducers and an image processor for receiving electrical signals from said ultrasound transducers of said catheter and processing said signals to construct an anatomic image of a portion of said heart, said location positioning system being operative for registering said operative location of said annuloplasty device with said anatomic image while said annuloplasty device is being inserted by said catheter based on location and orientation coordinates, said location positioning system being operative for locating points of interest on a left circumflex coronary artery of said heart whereby an operator can determine whether actuation of said annuloplasty device may compromise blood flow through said left circumflex coronary artery.

5. The apparatus according to claim 4, wherein said image processor is operative for processing said electrical signals to construct a plurality of 2-dimensional ultrasound images of said heart, and for combining said 2-dimensional ultrasound images into a 3-dimensional ultrasound image.

6. The apparatus according to claim 4, wherein said image processor is operative for constructing said anatomic image and registering said operative location of said annuloplasty device with said anatomic image concurrently with insertion of said annuloplasty device into said coronary sinus.

\* \* \* \* \*